(12) United States Patent
Hatzis et al.

(10) Patent No.: US 9,452,076 B2
(45) Date of Patent: Sep. 27, 2016

(54) FOOT SUPPORT DEVICE

(75) Inventors: Thomas V. Hatzis, Stamford, CT (US); Stan Wadolowski, Stamford, CT (US); Michael Cantore, Stamford, CT (US); Scott Axelrod, Wakefield, RI (US)

(73) Assignee: REBEL THERAPEUTICS, INC.CT (US)

(*) Notice: Subject to any disclaimer, the term of this patent is extended or adjusted under 35 U.S.C. 154(b) by 99 days.

(21) Appl. No.: 13/545,976

(22) Filed: Jul. 10, 2012

(65) Prior Publication Data

US 2013/0172801 A1 Jul. 4, 2013

Related U.S. Application Data

(60) Provisional application No. 61/508,045, filed on Jul. 14, 2011.

(51) Int. Cl.
*A61F 5/01* (2006.01)

(52) U.S. Cl.
CPC ............ *A61F 5/0127* (2013.01); *A61F 5/0113* (2013.01)

(58) Field of Classification Search
CPC . A61F 5/0113; A61F 5/0116; A63B 21/143; A63B 21/1449; A63B 23/085; A61H 1/0266
USPC .......... 602/23, 26–29; 128/882; 482/124, 79
See application file for complete search history.

(56) References Cited

U.S. PATENT DOCUMENTS

| | | | |
|---|---|---|---|
| 4,252,112 A | 2/1981 | Joyce | |
| 4,930,767 A * | 6/1990 | Hamm | A63B 21/0552 482/124 |
| 5,257,969 A * | 11/1993 | Mance | 602/28 |
| 5,399,155 A | 3/1995 | Strassburg | |
| 5,718,673 A | 2/1998 | Shipstead | |
| 5,799,659 A | 9/1998 | Stano | |
| 5,897,520 A | 4/1999 | Gerig | |
| 6,019,741 A | 2/2000 | Prieskorn | |
| 6,267,742 B1 | 7/2001 | Krivosha et al. | |
| 6,602,216 B1 | 8/2003 | Nordt, III | |
| 6,695,797 B2 | 2/2004 | Trieloff | |
| 6,755,798 B2 | 6/2004 | McCarthy et al. | |
| 7,175,574 B2 * | 2/2007 | Carmel | A63B 21/0004 482/124 |
| 7,182,743 B2 | 2/2007 | Slautterback | |
| 7,753,864 B2 * | 7/2010 | Beckwith et al. | 602/23 |
| 2004/0215123 A1 | 10/2004 | Slautterback | |
| 2008/0306422 A1 * | 12/2008 | McChesney et al. | A61F 5/0111 602/26 |
| 2010/0042032 A1 | 2/2010 | Tomczak | |

OTHER PUBLICATIONS

Simon & Schuster Handbook of Anatomy & Physiology of the Human Body, pp. 20, 21 & 25.

* cited by examiner

*Primary Examiner* — Kari Petrik (57) ABSTRACT

The present invention relates to a device for limiting plantarflexion of an ankle and thereby maintaining the plantar fascia in a neutral to slight dorsiflection. The device includes a foot assembly, tension members, and a leg strap. The leg strap, is adapted so that a portion of the leg strap is removable and can be engaged above the knee. In some embodiments of the present invention, the leg strap, includes at least one connection member for receiving the tension member wherein the connection member is affixed to the leg strap at or about the knee when the leg strap is engaged to the leg.

5 Claims, 7 Drawing Sheets

FOOT SUPPORT DEVICE

RELATED FILING(S)

Priority based on Provisional Application No. 61/508,045; Filing Date Jul. 14, 2011.

FIELD OF THE INVENTION

The invention relates to a foot support device. More specifically, the present invention relates to a foot support device for limiting plantar flexion of an ankle thereby maintaining the plantar fascia in a neutral to slight dorsiflexion. More specifically, the present invention relates to a foot support device wherein a tension is applied to the ball of the foot via a tension member removably engaged to at least a portion of the leg at or about the knee.

BACKGROUND OF THE INVENTION

The human foot and ankle contain 26 bones and more than 100 muscles, tendons, and ligaments. This complex structure receives the impact of each step experienced by an individual.

One source of heel pain commonly observed is due to a condition known as recalcitrant plantar fasciitis. Plantar fasciitis occurs in the plantar fascia, a fibrous membrane disposed longitudinally across the bottom of the foot. The plantar fascia is attached at the heel bone. The plantar fascia becomes broader and thinner as it extends longitudinally across the bottom of the foot, eventually dividing near the heads of the metatarsal bones into five processes, one for each of the five toes. The strongest ligament in the body, the plantar fascia's purpose is to protect the softer muscles and tissues of the bottom of the foot from injury, as well as to help maintain the integrity of the foot structure itself.

If the fascia becomes stretched or strained, the arch area becomes tender and swollen as well as the area about the heel bone. This inflammation is called plantar fasciitis and is typically painful from the heel throughout the arch up into the Achilles tendon. Patients suffering from this condition usually have relatively tight and inflexible heel cords, sometimes referred to as Achilles tendon tightness. When the heel cord is tight, it causes compensation in the foot with over pronation of the foot during weight bearing. The pain is consistently worse when you first get up in the morning and at the end of the day. The pain usually lurks in the heel pad and may include the arch ligament.

Plantar fasciitis is often caused by contracture of the Achilles tendon and the plantar fascia, which can occur at night during sleep, or during daytime inactivity. The Achilles tendon, the strongest and thickest tendon in the human body, begins at or about the middle of the posterior side of the leg extending downward towards the heel, narrowing as it progresses towards its point of insertion at the posterior surface of the os calcis. When an individual is standing, walking, running, or even sitting in a position in which the feet are in contact with the floor or other surface, both the plantar fascia and the Achilles tendon are extended to varying degrees depending of course on the nature and intensity of the activity. During sleep, an individual has a natural tendency to plantar flex the ankle joint beyond the position, which is normal during walking, standing, or sitting with one's feet on the floor. Plantar flexion is when the bottom of the foot is extended so as to form an angle with the lower leg of greater than 90 degrees, i.e., extend such that the forefoot moves away from the body. Dorsiflexion is the opposite motion, when the foot is moved to a position in which the bottom of the foot forms an angle with the lower leg of less than 90 degrees, i.e., such that the top of the foot moves toward the body.

Another condition, Achilles tendonitis can result from overuse of the tendon in sports activities, and can also result from a number of inflammatory diseases, of which rheumatoid arthritis is one.

For some time, a common method of treatment of plantar fasciitis and Achilles tendonitis has been the use of a night splint. The night splint typically consists, essentially, of a boot-like structure, which is strapped to a patient's lower leg and foot, holding the foot relative to the lower leg in a position such that the ankle joint is held in slight dorsiflexion. In so doing, both the plantar fascia and the Achilles tendon are slightly extended and are not allowed to contract during the night. The use of night splints together with the variety of other elements of treatment including anti-inflammatory medications, physical therapy, and foot cushions for use during the daytime, has proved beneficial in the treatment of plantar fasciitis.

Various braces and splints, sometimes referred to as night splints, are advertised for treatment of plantar fasciitis and/or Achilles tendonitis. These devices typically consist of a molded splint or a combination of molded plastic and metal framework, with the dorsiflexion set at, for example, about 5 degrees. Illustrative examples are disclosed in U.S. Pat. No. 5,399,155 (Strassburg et al.), U.S. Pat. No. 5,718,673 (Shipstead), U.S. Pat. No. 5,799,659 (Stano), U.S. Pat. No. 5,897,520 (Gerig), U.S. Pat. No. 6,019,741 (Prieskom), U.S. Pat. No. 6,267,742 (Krivosha et al.), U.S. Pat. No. 6,602,216 (Nordt, III), U.S. Pat. No. 6,695,797 (Trieloff), and U.S. Pat. No. 6,755,798 (McCarthy et al.), and U.S. Patent Application Publication Nos. 2004/0215123 (Slautterback et al.) and 2006/0064048 (Stano).

U.S. Pat. No. 7,753,864 (Beckwith et al.) discloses a foot support device that when worn maintains the plantar fascia and other structures on the plantar surface of the foot in a neutral to slight dorsiflexion under application of static tension. The Beckwith device includes (a) a calf strap removably engagable to the calf of a leg; (b) a foot assembly removably engagable to the foot of the leg such that when the device is worn the assembly can be positioned proximate to the ball of the foot intermediate to the midfoot and forefoot areas of the foot to secure it to the foot; and (c) a substantially inelastic tension member connectable between the calf strap and the foot assembly in a tensioned manner such that when the device is worn the plantar flexion of the ankle is limited such that the plantar surface of the foot is held in a neutral to slight dorsiflexion.

Although such known devices may hold the plantar fascia in neutral to slight dorsiflexion, there are a number of disadvantages to such devices.

One disadvantage of such known devices is that the calf strap is connected to the leg below the knee, thus generating a downward force on the calf. In this known device, a calf strap is connected to the foot assembly via a tension member. After the tension member is tightened, the foot is maintained in neutral to slight dorsiflexion. In known devices, the calf strap comprises a belt or strap. The belt is arranged such that it is secured around the upper calf of a leg. The user may adjust the size of the loop formed by the strap around the calf to maintain the calf strap in position while the device is in use.

One disadvantage of the calf strap configuration is that the calf muscle receives the tension force. This leads to discomfort for the user, especially during prolonged use of the foot support device.

Another disadvantage of the calf strap configuration is that it is difficult to maintain a secure engagement with the leg at the upper calf. This disadvantage leads to discomfort for the user. In addition, this disadvantage reduces the effectiveness of the known device because the calf strap tends to loosen during prolonged use. In such cases, the calf strap slides down the leg toward the foot, thus eliminating the tension force between the foot and the calf, and rendering the foot support device completely useless.

Another disadvantage of known foot support devices is that they use a single linear tension member to connect the calf strap and the foot assembly. This design prevents the user from making lateral adjustments to the tension in the foot support device.

What is desired, therefore, is a device for limiting plantar flexion of an ankle thereby maintaining the plantar fascia in a neutral to slight dorsiflexion. The desired device should include a removable foot assembly [FIG. 1, member 1] and can be engaged to the foot, a removable leg strap, which is part of the knee assembly, [FIG. 1, member 2] and can be engaged to at least a portion of the leg at or about the knee, and a tension member [FIG. 1, member 3] and connectable between the foot assembly [FIG. 1, member 1] and the tension member [FIG. 1, member 3] in a tensioned manner such that when the device is worn the plantar flexion of the ankle is limited.

SUMMARY OF THE INVENTION

Accordingly, it is an object of the present invention to provide a foot support for maintaining the foot in a neutral to slight dorsiflexion under application of static tension, wherein the foot assembly is connected to the leg at or about the knee.

It is another object of the present invention to provide a more comfortable foot support device.

It is another object of the present invention to provide a leg strap, which is part of the knee assembly, wherein a least a portion of the leg strap is removable and can be engaged at or about at least a portion of a knee.

Figure 2:
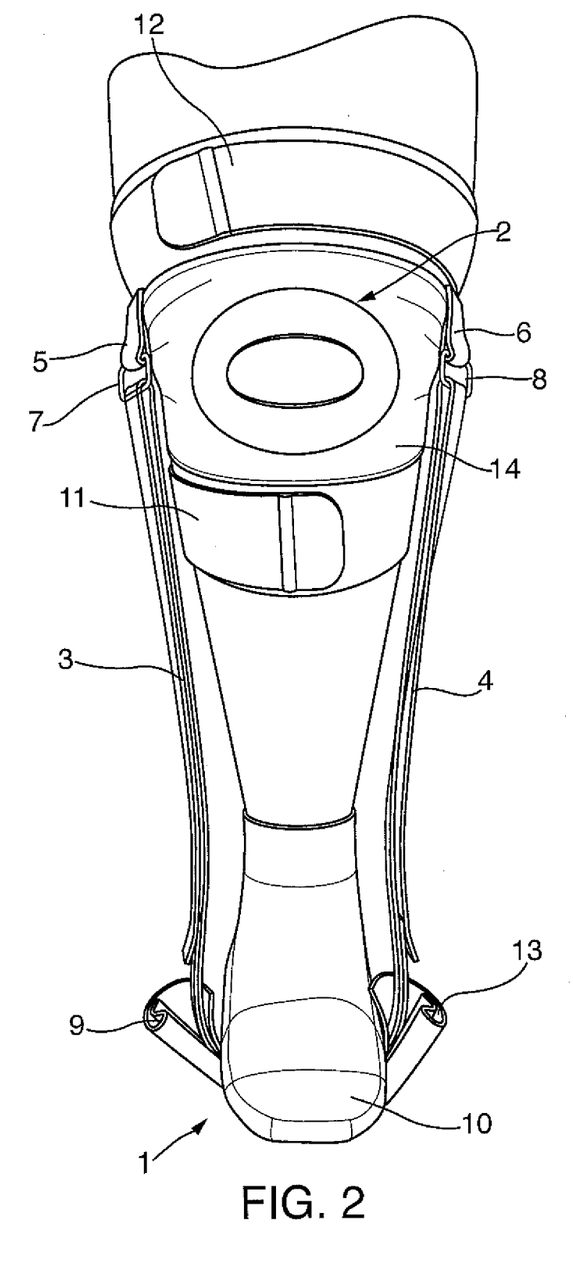
FIG. 2 illustrates a front view of the foot assembly [FIG. 2, member 1] of one embodiment of the present.
Figure 3:
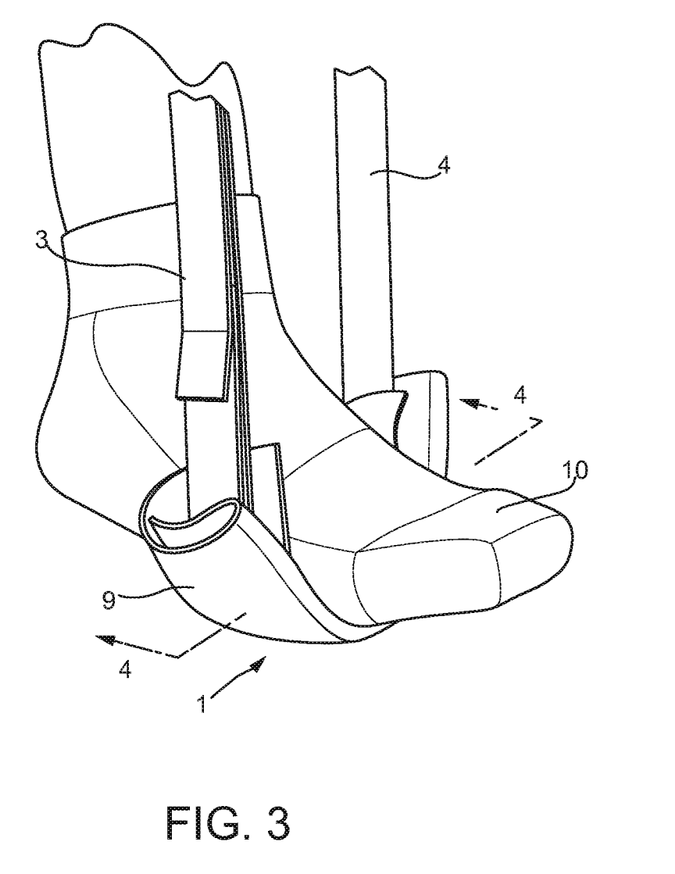
FIG. 3 illustrates a perspective view of one embodiment of the present invention wherein the first tension member [FIG. 3, member 3] and second tension member [FIG. 3 member 4] are parallel.
Figure 4:
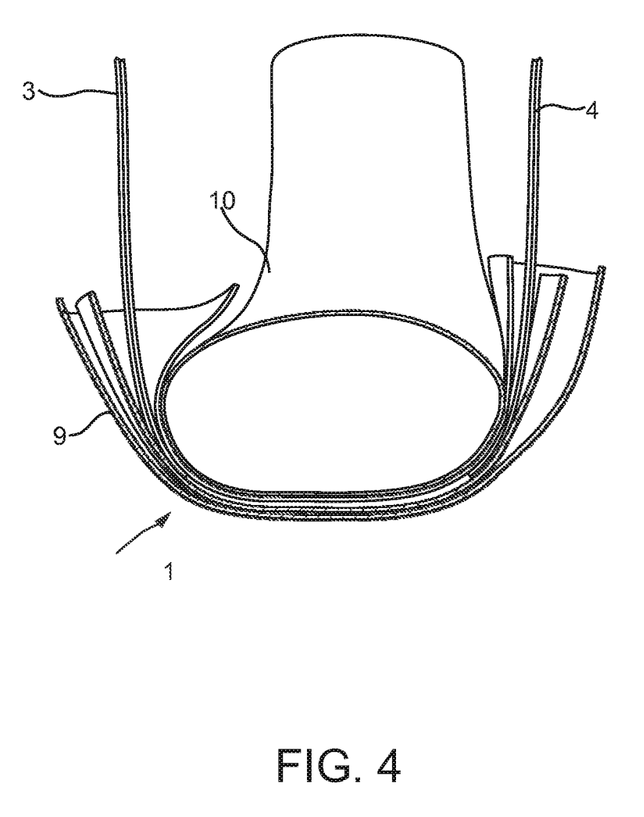
FIG. 4 illustrates a cross section of the one embodiment of the present invention shown in FIG. 2 wherein the first tension member [FIG. 2, member 3] and second tension member [FIG. 2, member 4] are parallel.
Figure 5:
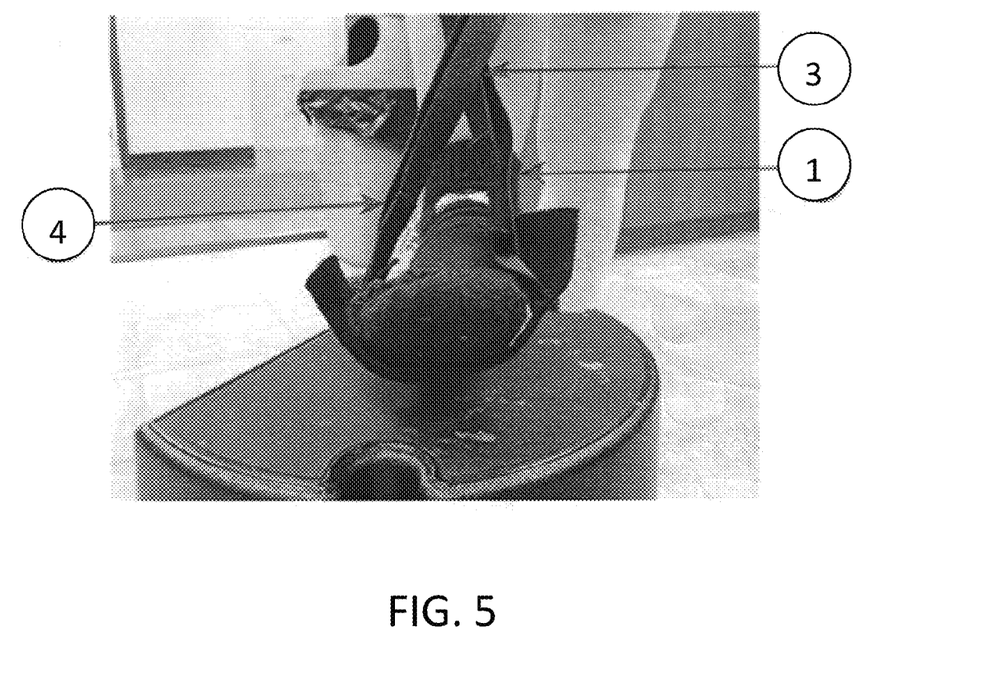
Figure 6:
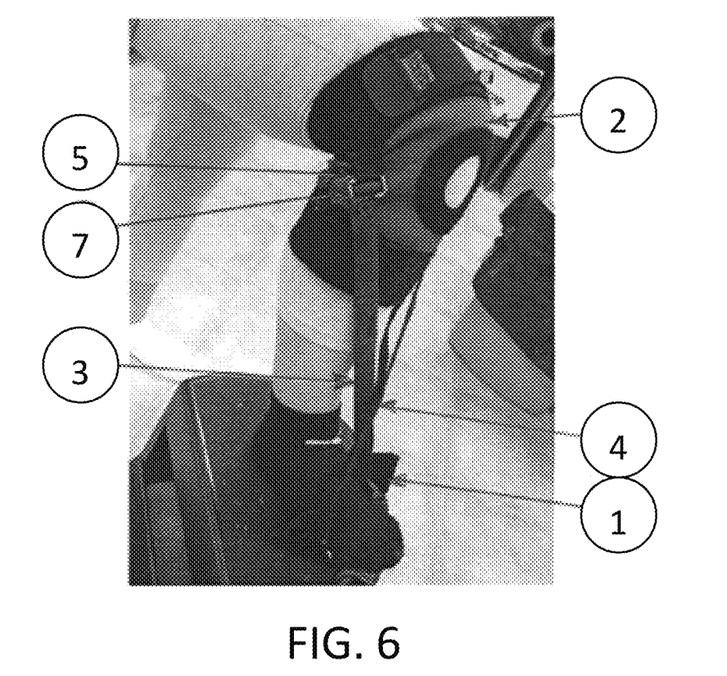
Figure 7:
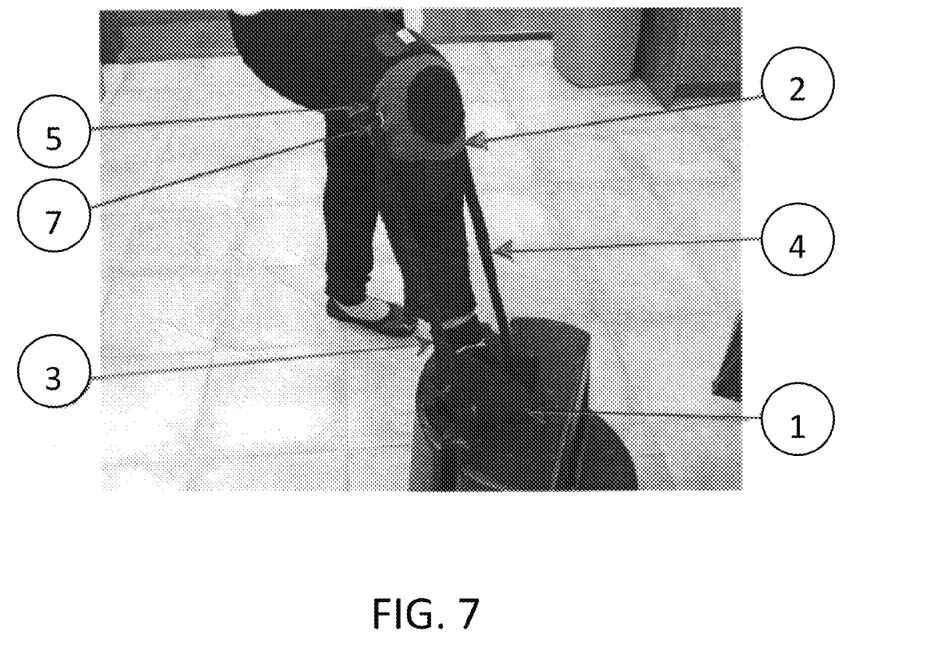

It is yet a further object of the present invention to provide a leg support device having two or more linear tension members [illustrated in FIG. 2, members 3 and 4], which are portions of a continuous strap, thereby providing an additional degree of customization of the static positioning of the device when worn.

In order to overcome the deficiencies of the prior art and to achieve at least some of the objects and advantages listed, the invention comprises a device for limiting plantar flexion of an ankle thereby maintaining the plantar fascia in a neutral to slight dorsiflexion. The device comprises a removable foot assembly and can be engaged to a foot of a leg, a knee assembly having a removable leg strap and can be engaged to the leg at or about a knee of said leg, and a tension member which are portions of a single continuous strap, connectable between the foot assembly and the leg strap, which is part of the knee assembly, in a tensioned manner such that when the device is worn the plantar flexion of the ankle is limited. [See for example FIG. 1, members 1-4].

Figure 1:
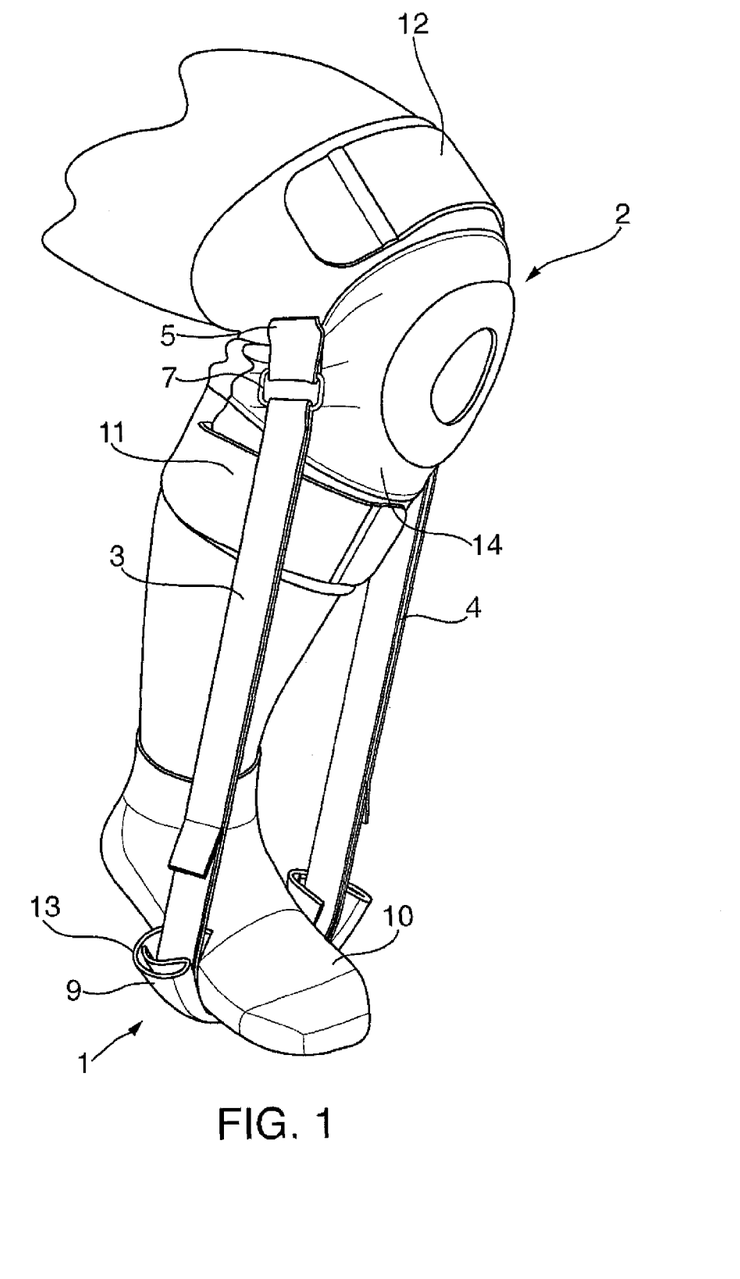
FIG. 1 illustrates a perspective view of one embodiment of the present invention.

In some embodiments of the present invention a portion of the leg strap, which is part of the knee assembly [e.g. FIG. 1 member 2] is removable and can be engaged above the knee, while the remaining portion of the knee assembly [member 2] can be engaged below the knee. In some embodiments of the present invention, the knee assembly [member 2], is configured such that it is similar to a knee brace in that it comprises at least two leg straps that wrap around the leg, one above the knee [leg strap 12] and one below the knee [leg strap 11], and a material section 14 interconnecting leg strap 12 to leg strap 11 as is shown in FIGS. 1 and 2. In this manner the knee assembly [FIG. 1, member 2] is removable and engages the leg at or about the knee.

In yet other embodiments of the present invention the foot support device comprises a foot assembly [FIG. 2, member 9] arranged such that the tension force is directed to the ball of the foot, thereby limiting the plantar flexion of the ankle.

In yet further embodiments of the present invention, the tension members are comprised of at least two linear members extending between the foot assembly [FIG. 1, member 1] and the leg strap, which is part of the knee assembly, [FIG. 1, member 2], said two linear members which are portions of a single continuous strap, extending below the foot through a guide member [FIG. 2, member 9]. In some embodiments, the at least two linear members are parallel between the foot assembly [FIG. 1, member 1] and the leg strap, which is part of the knee assembly, [FIG. 1, member 2]. In yet other embodiments, the present invention comprises at least two linear tension members that are portions of a single continuous tension member [FIG. 2, members 3 and 4] which may be parallel between the foot assembly [FIG. 2, member 1] and the knee assembly, [FIG. 2, member 2]. As is apparent to one of ordinary skill in the art, the two linear tension members which are portions of a single continuous tension member [FIG. 2, members 3 and 4] may cross each other at any point between the knee assembly and the foot assembly while maintaining tension force directed to the ball of the foot, limiting plantar flexion of the ankle.

The embodiments of this invention achieve the objective of maintaining a stable foot position without the tension caused by the "tourniquet" or tightness required by other devices to maintain the foot in a stable desired position. Tightness around the leg constricts blood circulation causing discomfort and discouraging the use of a foot stabilizing device for any extended period of time. In sharp contrast, the embodiments of this invention do not employ such blood constricting tightness and thereby enable the continuous use of this device for much longer periods of time.

DETAILED DESCRIPTION OF THE INVENTION

In reference to FIG. 1, one embodiment of the present invention is shown. The device comprises at least three elements: (a) a foot assembly [FIG. 1, member 1], (b) a tension assembly comprising two tension members [FIG. 1 member 3 and member 4], and (c) a knee assembly [FIG. 1, member 2]. The knee assembly, [FIG. 1, member 2] comprises a brace for the knee formed by the upper leg strap 12, the lower leg strap 11 and the interconnecting material section 14. The brace has an upper portion, represented by the leg strap [FIG. 1, member 12], that is removably engaged to the leg above the knee, and a lower portion, represented by the leg strap [FIG. 1, member 11], that is removably engaged to the leg below the knee. The upper portion and the lower portion of the brace both comprise a strap that is engaged around the leg and held in place by a hook and loop fastener.

It will be understood by a person having ordinary skill in the art that the leg strap, which is part of the knee assembly, [FIG. 1, member 2] may take many different forms as long as it is designed to engage with at least a portion of the leg above the knee and below the knee. In the embodiment shown in FIG. 1, the brace is made from synthetic fabric. It will be understood by a person having ordinary skill in the art that any known material may be used to construct the leg strap, which is part of the knee assembly, [FIG. 1, member 2].

In further reference to the embodiment of the present invention shown in FIG. 1, the leg strap, which is part of the knee assembly, [FIG. 1, member 2] includes at least one connection point. In the embodiment shown in FIG. 2 the leg strap, which is part of the knee assembly, [FIG. 1, member 2] includes two connection points [FIG. 2, members 5 and 6) wherein the securing material connects to opposite sides of the leg strap. The opposite points at which the securing material connects to the leg strap, which is part of the knee assembly, provide stability in the ankle and uniform tension on both sides of the foot.

The connection point comprises a rigid loop [FIG. 1, member 7] that is fastened to the brace by a piece of material [FIG. 1, member 5] secured thereto. The connection point is fastened to the leg strap, which is part of the knee assembly, [FIG. 1, member 2] such that tension force is transferred to a portion of the leg above the knee. The embodiment shown in FIG. 2 includes a symmetrically arranged fastener on the opposite side of the leg strap, which is part of the knee assembly, [FIG. 2, member 6]. Thus, when the foot support device is in use, the tension force is applied to a portion of the leg above the knee, thereby providing a more stable and comfortable configuration.

FIG. 2 illustrates a front view of the foot assembly [FIG. 2, member 1] of one embodiment of the present invention. In the embodiment shown, the foot assembly [FIG. 2, member 1] comprises a sock [FIG. 2, member 10] in combination with a guide member [FIG. 2, member 9] for receiving the tension member [FIG. 2, members 3 and 4]. The guide member [FIG. 2, member 9] is fixed to the bottom of the sock [FIG. 2, member 10] proximate to the ball of the foot. The guide member [FIG. 2, member 9] may be fixed to the sock [FIG. 2, member 10] with adhesive, stitching, or any other known method.

The guide member [FIG. 2, member 9] is arranged such that it can receive the tension members [FIG. 2 members 3 and 4]. In the embodiment shown, the tension members [FIG. 2 members 3 and 4] are interconnected to one another to form a single strap which is fed through the passageway 13 in the guide member [FIG. 2, member 9] such that the tension members [FIG. 2 members 3 and 4] pass under the ball of the foot. While in use, the force on the tension members [FIG. 2 members 3 and 4] is increased and the plantar fascia is maintained in a neutral to slight dorsiflexion.

It will be understood by a person of ordinary skill in the art that many different foot assemblies are possible. For example, the guide member [FIG. 2, member 9] may be fastened to different areas of the sock [FIG. 2, member 10]. In some embodiments a sock [FIG. 2, member 10] is not necessary. In some embodiments the tension member [FIG. 2, members 3 and 4] is connected to the foot assembly [FIG. 2, member 1] by some other known means. In some embodiments the tension members [FIG. 2, members 3 and 4] are connected to the toe of the foot. In yet other embodiments of the present invention, the tension members [FIG. 2, member 3 and 4] are connected to the top of the sock [FIG. 2, member 10].

The arrangement of the foot assembly [FIG. 2, member 1] disclosed in the figure is preferred for a number of reasons. First, the sock [FIG. 2, member 10] increases the comfort of the user. Second, the fact that the guide member [FIG. 2, member 9] is secured to the bottom of the sock [FIG. 2, member 10] proximate to the ball of the foot is preferred because it concentrates the tension force at the ball of the foot. Third, the foot assembly [FIG. 2, member 1] is made from materials that can be easily cleaned.

In reference to FIG. 2, a front view of an embodiment of the present invention is shown. In this embodiment the tension member [FIG. 2, members 3 and 4] comprises two linear members that are portions of one continuous strap that extends from the foot assembly [FIG. 2, member 1] to the leg strap, which is part of the knee assembly, [FIG. 2, member 2]. Each linear strap is secured to the leg strap, which is part of the knee assembly, [FIG. 2, member 2] via a connection point. In the embodiment shown, the linear members are each looped through a buckle and secured using a hook and loop fastener. The user can tighten the tension members [FIG. 2, members 3 and 4] by pulling the tension member [FIG. 2, members 3 and 4] further through the buckle and securing its end via a hook and loop fastener. In the embodiment shown in FIG. 2, the tension members [FIG. 2, members 3 and 4] are parallel. In some embodiments, it is preferred that the tension members [FIG. 2, members 3 and 4] are crossed. In most embodiments it is preferred that the tension members comprise a single continuous member fed through a guide member below the ball of the foot as illustrated in FIG. 2. In reference to the embodiment shown in FIG. 2, the tension members [FIG. 2, members 3 and 4] are secured to the leg strap, which is part of the knee assembly, [FIG. 2, member 2] such that the great majority of the tension force applied to the leg via the brace is applied above the knee.

It should be understood that the foregoing is illustrative and not limiting, and that obvious modifications may be made by those skilled in the art without departing from the essence of the invention.

What is claimed is:

1. A device adapted for attachment to a leg of a human for therapeutically treating plantar fasciitis in a foot in said leg by controllably maintaining dorsiflexion of the plantar fascia, said device comprising:

a foot assembly comprising a sock, adapted for placement over the foot in said leg to which the device is being attached, and a guide member affixed to the sock proximate a ball of the foot with said guide member, upon attachment of said device to the leg, forming a passageway extending under the ball of the foot in said leg;

a knee assembly comprising a first leg strap for removable engagement to a knee such that the first leg strap of the knee assembly is adapted for location above a kneecap of the knee in said leg, a second leg strap for removable engagement to the leg such that the second leg strap of the knee assembly is adapted for location below the kneecap of the knee in said leg and a material section interconnecting the first leg strap to the second leg strap such that upon attachment of the device to said leg the knee assembly forms a brace for the knee which engages and surrounds the knee; and a tension assembly for connecting said foot assembly to said knee assembly in a tensioned manner on each opposite side of said leg wherein said tension assembly comprises a tension member disposed on each opposite side of said knee assembly with each tension member interconnecting the foot assembly to the knee assembly to form a single strap passing in one continuous loop from one side of the knee assembly through the passageway in said guide member under said ball of the foot to the opposite side of said knee assembly, with the single strap being connected through a buckle fixedly attached to the knee assembly and located at a position between the first leg strap and the second leg strap of the knee assembly and adapted for placement on said one side of said leg adjacent to a rotatable joint in the knee to enable the tension in said single strap to be adjusted by tightening the connection between said single strap and said buckle wherein when the device is worn dorsiflexion of the plantar fascia is controllably maintained.

2. The device of claim 1 wherein said single strap is connected to a second buckle located on said opposite side of said knee assembly between the first leg strap and the second leg strap, the second buckle adapted for placement adjacent to the rotatable joint in the knee for adjusting tension in said single strap.

3. The device of claim 2 wherein said knee assembly has an opening through which the kneecap in said knee is adapted to be exposed when the device is attached to the leg.

4. The device of claim 2 wherein the single strap passes through the passageway in the guide member and is adapted to pass under the ball of the foot to form said continuous loop between opposite sides of the knee assembly permitting tension in the strap to be adjusted by tightening the connection between the second buckle and the strap.

5. The device of claim 1 wherein the knee assembly further comprises a securing material adapted to be located adjacent the kneecap for coupling said buckle in said tension assembly to said knee assembly with the buckle adapted to lie on said one side of the leg lateral to the kneecap at the rotatable joint of the knee.

* * * * *